(12) United States Patent
Tokuyama et al.

(10) Patent No.: US 8,479,886 B2
(45) Date of Patent: Jul. 9, 2013

(54) LUBRICATION-CONDITION DETECTOR, LUBRICANT FEEDER, INJECTION MOLDING MACHINE AND METHOD OF DETECTING LUBRICATION-CONDITION

(75) Inventors: Harumichi Tokuyama, Odawara (JP); Masahiko Mori, Tagata-Gun (JP); Makoto Takami, Ito (JP); Haruhiko Kikuchi, Numazu (JP); Akira Yoshinaga, Numazu (JP); Noriyuki Sasaki, Numazu (JP); Shinya Itani, Mishima (JP)

(73) Assignee: Toshiba Kikai Kabushiki Kaisha, Tokyo (JP)

( * ) Notice: Subject to any disclaimer, the term of this patent is extended or adjusted under 35 U.S.C. 154(b) by 1030 days.

(21) Appl. No.: 12/100,825

(22) Filed: Apr. 10, 2008

(65) Prior Publication Data

US 2008/0271949 A1    Nov. 6, 2008

(30) Foreign Application Priority Data

Apr. 11, 2007  (JP) .................. 2007-103773

(51) Int. Cl.
  *F01M 1/18*  (2006.01)
(52) U.S. Cl.
  USPC .............................. 184/6.4; 184/6
(58) Field of Classification Search
  USPC .............................. 184/6.1, 6.4, 7.4, 105.1, 6
  See application file for complete search history.

(56) References Cited

U.S. PATENT DOCUMENTS

| | | | |
|---|---|---|---|
| 4,326,603 A * | 4/1982 | Darrow et al. ................. | 184/6.1 |
| 4,632,223 A | 12/1986 | Maurer et al. | |
| 5,217,662 A | 6/1993 | Yamamura | |
| 6,125,969 A * | 10/2000 | Graf et al. ................... | 184/105.1 |
| 6,779,997 B2 * | 8/2004 | Kappelmuller ............... | 425/107 |
| 7,725,211 B2 * | 5/2010 | Ludwig ......................... | 700/200 |

FOREIGN PATENT DOCUMENTS

| | | |
|---|---|---|
| DE | 33 38 420 | 5/1985 |
| DE | 690 09 444 | 9/1994 |
| JP | 60-109699 | 6/1985 |
| JP | 03-079325 | 4/1991 |
| JP | 05-111935 | 5/1993 |
| JP | 11-287395 | 10/1999 |
| JP | 2001-252956 | 9/2001 |
| JP | 2003-176830 | 6/2003 |

(Continued)

OTHER PUBLICATIONS

Office Action issued in German Appl 10 2008 018 285.0-26 on Nov. 11, 2010.

(Continued)

*Primary Examiner* — William E Dondero
*Assistant Examiner* — Robert T Reese
(74) *Attorney, Agent, or Firm* — DLA Piper LLP (US)

(57) ABSTRACT

A lubrication-condition detector detects a lubricant shortage of a target portion that repeats a predetermined operation at a predetermined cycle. The lubrication-condition detector includes: a physical-quantity measuring unit for continuously measuring a physical quantity related to the target portion; and a computer for determining a presence of a lubricant shortage based on the physical quantity. The computer includes: a cycle extractor for extracting a cycle datum per an operational cycle from continuous data including the physical quantity and its measuring time; a representative-value calculator for calculating a representative value for each of plural cycle data; and determining unit for determining a presence of a lubricant shortage based on the plural representative values.

20 Claims, 4 Drawing Sheets

FOREIGN PATENT DOCUMENTS

| | | |
|---|---|---|
| JP | 2005-054828 | 3/2005 |
| JP | 2005-164314 | 6/2005 |
| JP | 2005-351363 | 12/2005 |

OTHER PUBLICATIONS

English Translation of Office Action issued in German Appl 10 2008 018 285.0-26 on Nov. 11, 2010.
English Translation of JP-2003-176830 published Jun. 27, 2003.
English Translation of JP-2005-351363 published Dec. 22, 2005.
English Translation of JP-2005-164314 published Jun. 23, 2005.
English Abstract of DE 3338420 published May 2, 1985.
English Abstract of DE 69009444 published Apr. 15, 1994.
English Abstract of JP-2003-176830.
English Abstract of JP-2005-351363.
English Abstract of JP-2005-164314.
Japanese Office Action issued in JP 2007-103773 on Aug. 30, 2011.
English Language Translation of Japanese Office Action issued in JP 2007-103773 on Aug. 30, 2011.
Enalish Language Abstract of JP 2001-252956 published on Sep. 18, 2011.
English Language Translation of JP 2001-252956 published on Sep. 18, 2011.
English Language Abstract of JP 05-111935 published May 7, 1993.
English Language Translation of JP 05-111935 published May 7, 1993.
Engfish Language Abstract of JP 11-287395 published Oct. 19, 1999.
English Language Translation of JP 11-287395 published Oct. 19, 1999.
English Language Abstract of JP 2005-054828 published on Mar. 3, 2005.
English Language Translation of JP 2005-054828 published on Mar. 3, 2005.
English Language Abstract of JP 03-079325 published Apr. 4, 1991.

\* cited by examiner

LUBRICATION-CONDITION DETECTOR, LUBRICANT FEEDER, INJECTION MOLDING MACHINE AND METHOD OF DETECTING LUBRICATION-CONDITION

BACKGROUND OF THE INVENTION

1. Field of the Invention

The present invention relates to a lubrication-condition detector, a lubricant feeder, an injection molding machine including the same and a method of detecting lubrication condition.

2. Description of Related Art

There have been known injection molding machines for injecting melt of a resin or a metal into dies for molding. Many machine tools such as the injection molding machines include a driving mechanism that repeats a predetermined operation at a predetermined cycle.

In an exemplary arrangement of an injection molding machine, an injection shaft accommodated inside a cylinder is axially reciprocated to inject a molding material having been supplied into the cylinder.

Such a driving mechanism, which generally includes bearing(s) and ball screw(s), uses a lubricant for preventing frictions and rusts, cooling and the like.

A lubricant is degraded by a long time use to deteriorate the lubricity. A lubricity shortage on bearings and ball screws may cause heating, noises, vibrations or the like. If the driving is continued with the lubricity shortage, burning or the like may arise.

In order to avoid such problems, a lubricant feeder according to a known arrangement regularly feeds the lubricant in accordance with a driving time of the machine tool and the number of operations of the driving mechanism.

However, in general, not only a single driving mechanism requires the lubricant but also plural driving mechanisms may require suitable feed of the lubricant. Since such plural driving mechanism are different from one another in operation frequency and ranges of movement, a rate at which the lubricant is degraded varies depending on the driving mechanisms. Accordingly, it has been highly difficult to feed the lubricant to all the driving mechanisms without excess or shortage.

When the lubricant feed is in shortage (e.g., the lubricant feed is a small amount), the above-described problems may arise. On the other hand, when a large amount of the lubricant is fed, excessive lubricant may leak out of the driving mechanism(s) to cause pollution around the driving mechanism(s).

In view of the above problems, a grease supplier disclosed in Document 1 (JP-A-2003-176830) monitors values of electric characteristics between an outer ring and inner ring of a bearing (i.e., driving mechanism) and determines lubrication condition based on the monitored values so as to supply grease thereto.

The grease supplier according to Document 1, which supplies the grease based on the lubrication condition, can supply the grease without excess or shortage.

However, the grease supplier according to Document 1 is not intended to be applied to a driving mechanism that repeats a predetermined operation at a predetermined cycle. Thus, the grease supplier may not be able to suitably determine lubrication condition of a driving mechanism that repeats a cycle operation.

Values of electric characteristics between an outer ring and inner ring of a bearing that repeats a cycle operation are not continuous but exhibit transition as exemplarily shown in FIG. 3.

In the graph of FIG. 3, the vertical scale represents value(s) of electric characteristics while the horizontal scale represents time.

A period A shown in FIG. 3 represents changes of the value(s) of electric characteristics when the lubrication condition is favorable. Since the driving mechanism repeats a predetermined operation at a predetermined cycle (time T), a similar waveform of the electric characteristics values is repeatedly observed per time T.

In a period B, continuous driving of the driving mechanism for a long time degrades the lubricant and deteriorates the lubricity, such that the waveform of the electric characteristics values repeated per time T is gradually changed.

Then, as exemplarily shown in a period C, the waveform starts to be turbulent.

In the case described above, the grease supplier according to Document 1 determines that the lubricant is in shortage when the values of electric characteristics are out of a predetermined range. In other words, the grease supplier according to Document 1 uses only the maximum value or the minimum value in the waveform of the electric characteristics values repeated per time T so as to determine the lubrication condition.

Accordingly, for instance, when the waveform is so greatly turbulent that the lubricant may be in shortage although the minimum value or the maximum value of the electric characteristics values during time T is not greatly varied, the grease supplier according to Document 1 may not be able to suitably supply the grease.

In addition, in some exemplary cases, although the values of the electric characteristics are observed to be out of the predetermined range, the observed values may be determined to be accidental in comparison with the waveforms of preceding and subsequent cycles, such that it can be properly considered that the lubrication condition is favorable. Even in such cases, the grease supplier according to Document 1 may determine that the lubrication condition is unfavorable and supply the grease in an excessive amount.

SUMMARY OF THE INVENTION

An object of the present invention is to provide a lubrication-condition detecting method and a lubrication-condition detector that are capable of precisely detecting a lubricant shortage of a target portion that repeats a cycle operation, a lubricant feeder including the lubrication-condition detector and being capable of feeding a lubricant without excess or shortage, and an injection molding machine including the lubricant feeder.

A lubrication-condition detector according to an aspect of the present invention is for detecting a lubricant shortage of a target portion, the target portion including: a fixed member; a movable member that repeats a predetermined operation relative to the fixed member at a predetermined cycle; a driver that drives the movable member; and a lubricant that lubricates the movable member between the fixed member and the movable member, the lubrication-condition detector including: a physical-quantity measuring unit that continuously measures a physical quantity related to the target portion; and a computer that determines a presence of a lubricant shortage of the target portion based on the physical quantity measured by the physical-quantity measuring unit, in which the computer includes: a cycle extractor that extracts cycle data per operational cycle of the movable member from continuous data including the physical quantity measured by the physical-quantity measuring unit and a measuring time thereof; a representative-value calculator that calculates plural representative values respectively for plural cycle data extracted by the cycle extractor; and a determining unit that determines a presence of a lubricant shortage of the target portion based on the plural representative values calculated by the representative-value calculator.

According to the aspect of the present invention, the physical-quantity measuring unit continuously measures the physical quantity related to the target portion, such that the computer determines a presence of the lubricant shortage in the target portion based on the physical quantity having been measured.

Specifically, the cycle extractor of the computer extracts the cycle datum per operation cycle of the movable member from the continuous data including the physical quantity and the measuring time thereof, such that the representative-value calculator calculates the representative values respectively for the plural cycle data. The determining unit determines the presence of the lubricant shortage in the target portion based on the representative values.

By suitably setting the representative values and determination standard that reflect the lubrication condition of the target portion, the lubricant shortage can be precisely detected based on the changes of the physical quantity corresponding to the operational cycles of the movable member.

Examples of the representative values are the maximum value, the minimum value, an average value, an effective value, a variation value or the like of the physical quantity in the cycle data.

Although the grease supplier according to Document 1 also determines the lubrication condition based on the minimum value or the maximum value of the physical quantity, the grease supplier is different from the lubrication-condition detector according to the present invention in that the grease supplier does not extract the cycle data and that the grease supplier determines the lubricant shortage based on single data.

Since the grease supplier according to Document 1 does not extract the cycle data but makes a determination based on single data, the grease supplier cannot make a precise determination, for instance, when the time-series waveform of the electric characteristics values is so greatly turbulent that the lubricant may be in shortage although the minimum value or the maximum value of the electric characteristics values is not greatly varied, or when, although the values of the electric characteristics are observed to be out of the predetermined range, the observed values are determined to be accidental in comparison with the waveforms of preceding and subsequent cycles.

In contrast, since the lubrication-condition detector according to the present invention determines the presence of the lubricant shortage of the target portion based on the plural representative values calculated from the plural cycle data, the lubricant shortage of the target portion, which repeats cycle operation(s), can be precisely detected even in such cases as descried above.

According to the aspect of the present invention, it is preferable that the determining unit determines a presence of a lubricant shortage of the target portion based on time-series transition of the representative values of continuous plural cycles.

According to the aspect, since the determining unit determines the presence of the lubricant shortage in the target portion based on the time-series transition of the representative values of the continuous plural cycles, the lubricant shortage can be more precisely detected.

An exemplary method of determining the lubricant shortage is to determine a presence of a lubricant shortage when a representative value is observed to be greatly different from the preceding representative values or when the representative values greatly vary during a predetermined time.

According to the aspect of the present invention, it is preferable that the physical quantity measured by the physical-quantity measuring unit is electric current, electric resistance or electric potential difference between the fixed member and the movable member of the target portion.

According to the aspect, since the physical-quantity measuring unit measures electric current, electric resistance or electric potential difference between the fixed member and the movable member, the lubricant shortage can be precisely detected based on the above element.

In an exemplary arrangement where the target portion is a bearing while the fixed member (outer ring or inner ring) and the movable member (inner ring or outer ring) are metallic, the fixed member and the movable member are directly in contact with each other when the members are not driven, thereby exhibiting small electric resistance. On the other hand, when the members are driven, the lubricant infiltrates between the fixed member and the movable member, such that the fixed member and the movable member are insulated, thereby exhibiting large electric resistance.

However, when degraded, the lubricant becomes less infiltrative between the fixed member and the movable member, such that the electric resistance remains small even when the members are driven.

In other words, since the electrical resistance reflects the lubrication condition of the target portion, the lubricant shortage can be detected based on the electric resistance.

According to the aspect of the present invention, it is preferable that the driver of the target portion comprises a motor for operating the movable member, and the physical value measured by the physical-quantity measuring unit is torque or electric current of the motor.

According to the aspect, since the physical-quantity measuring unit measures the torque or the electric current of the motor, the lubricant shortage can be precisely detected based on the above element.

When the lubricant is degraded and the lubrication of the target portion is accordingly in shortage, friction resistance between the fixed member and the movable member is increased, thereby increasing the torque of the motor driving the movable member.

In other words, since the torque of the motor reflects the lubrication condition of the target portion, the lubricant shortage can be detected based on the torque.

Alternatively, since the electric current for driving the motor is varied when the friction resistance between the fixed member and the movable member is increased, the electric current of the motor reflects the lubrication condition of the target portion. Thus, the lubricant shortage can be detected based on the electric current.

A lubricant feeder according to another aspect of the present invention includes the above-described lubrication-condition detector; and a feeder that feeds the lubricant to the target portion when the lubrication-condition detector detects a lubricant shortage of the target portion.

According to the aspect of the present invention, when the lubrication-condition detector detects the lubricant shortage of the target portion, the feeder feeds the lubricant to the target portion.

The lubricant feeder, since including the above-described lubrication-condition detector, can precisely detects the lubricant shortage of the target portion. Additionally, the feeder can feed the lubricant without excess or shortage based on the detection of the lubricant shortage by the lubrication-condition detector.

Accordingly, the lubricant feeder according to the aspect of the present invention can prevent problems such as heating, noises, vibration and burning of the target portion due to the lubricant shortage and pollution with the excessive lubricant around the target portion.

According to the aspect of the present embodiment, it is preferable that the lubrication-condition detector separately detects lubricant shortages of plural target portions, and the feeder feeds the lubricant only to a target portion where a lubricant shortage is detected among the plural target portions.

According to the aspect of the present invention, the lubrication-condition detector detects the lubricant shortage of the plural target portions separately, and the feeder feeds the lubricant only to the target portion(s) in which the lubricant shortage is detected.

Hence, even when the lubricant feeder according to the present invention is applied to, for instance, a machine tool that includes plural portions to be detected, the lubricant can be fed to the plural portions without excess or shortage.

According to the aspect of the present invention, the above-described lubricant feeder preferably further includes an alarm notifier that notifies a lubricant shortage(s) of the target portion(s) detected by the lubrication-condition detector by an alarm.

According to the aspect, the alarm notifier notifies the lubricant shortage of the target portion(s) detected by the lubrication-condition detector by an alarm.

Thus, the lubricant feeder according to the present invention can notify and warn an operator of the lubricant shortage by an alarm.

For instance, even when the lubricant shortage is detected by the lubrication-condition detector, the feeder may not be able to feed the lubricant thereto when no lubricant is stored in the lubricant feeder. In such a case, the alarm notifier continues to notify and alarm an operator for a long time. When noticing that alarm is continuously activated without cancellation, the operator can check the lubricant feeder and supply the lubricant into a storage container or the like of the lubricant feeder, thereby preventing problems such as burning, heating, noises and vibration.

The alarm notifier may not necessarily issue an alert immediately after the lubrication-condition detector detects the lubricant shortage of the target portion but may issue an alarm when the lubricant shortage is continuously detected for a predetermined time period.

With this arrangement, while no alarm is issued when the feeder feeds the lubricant and solves the lubricant shortage, an alarm can be issued only when problems of burning, heating, noises and vibration may be caused due to the continuous lubricant shortage for a long time.

An injection molding machine according to still further aspect of the present invention includes the above-described lubricant feeder.

According to the aspect, the lubricant feeder can feed the target portion(s) of, for instance, a driving mechanism of the injection molding machine with the lubricant without excess or shortage, thereby preventing problems such as burning, heating, noises and vibration of the driving mechanism and the like due to the lubricant shortage.

A method of detecting lubrication condition according to still further aspect of the present invention is for detecting a lubricant shortage of a target portion, the target portion including: a fixed member; a movable member that repeats a predetermined operation relative to the fixed member at a predetermined cycle; a driver that drives the movable member; a lubricant that lubricates the movable member between the fixed member and the movable member, the method including: continuously measuring a physical quantity related to the target portion; extracting a cycle datum per operational cycle of the movable member from continuous data including the measured physical quantity and a measuring time thereof; calculating a representative value for each of extracted plural cycle data; and determining a presence of a lubricant shortage of the target portion based on the calculated plural representative values.

According to the aspect, the physical quantity related to the target portion is continuously measured and the cycle datum per operational cycle of the movable member is extracted from the continuous data including the physical quantity and the measuring time thereof. Then, the representative values respectively for the plural cycle data are calculated, and a presence of the lubricant shortage of the target portion is determined based on the calculated representative values.

By suitably setting the representative values and determination standard that reflect the lubrication condition of the target portion, the lubricant shortage can be precisely detected based on the changes of the physical quantity corresponding to the operational cycles of the movable member.

According to the aspect of the present invention, it is preferable that the presence of a lubricant shortage of the target portion is determined based on time-series transition of the representative values of continuous plural cycles.

According to the aspect, since the presence of the lubricant shortage in the target portion is determined based on the time-series transition of the representative values of the continuous plural cycles, the lubricant shortage can be precisely detected.

According to the aspect of the present invention, it is preferable that the measured physical quantity is electric current, electric resistance or electric potential difference between the fixed member and the movable member of the target portion.

According to the aspect, since electric current, electric resistance or electric potential difference between the fixed member and the movable member is measured, the lubricant shortage can be precisely detected based on the above element.

According to the aspect of the present invention, it is preferable that the driver of the target portion includes a motor for operating the movable member, and the measured physical value is torque or electric current of the motor.

According to the aspect, since the torque or the electric current of the motor is measured, the lubricant shortage can be precisely detected based on the above element.

DETAILED DESCRIPTION OF PREFERRED EMBODIMENT(S)

An embodiment of the present invention will be described below in reference to attached drawings.

[Arrangement of Injection Molding Machine]

Figure 1:
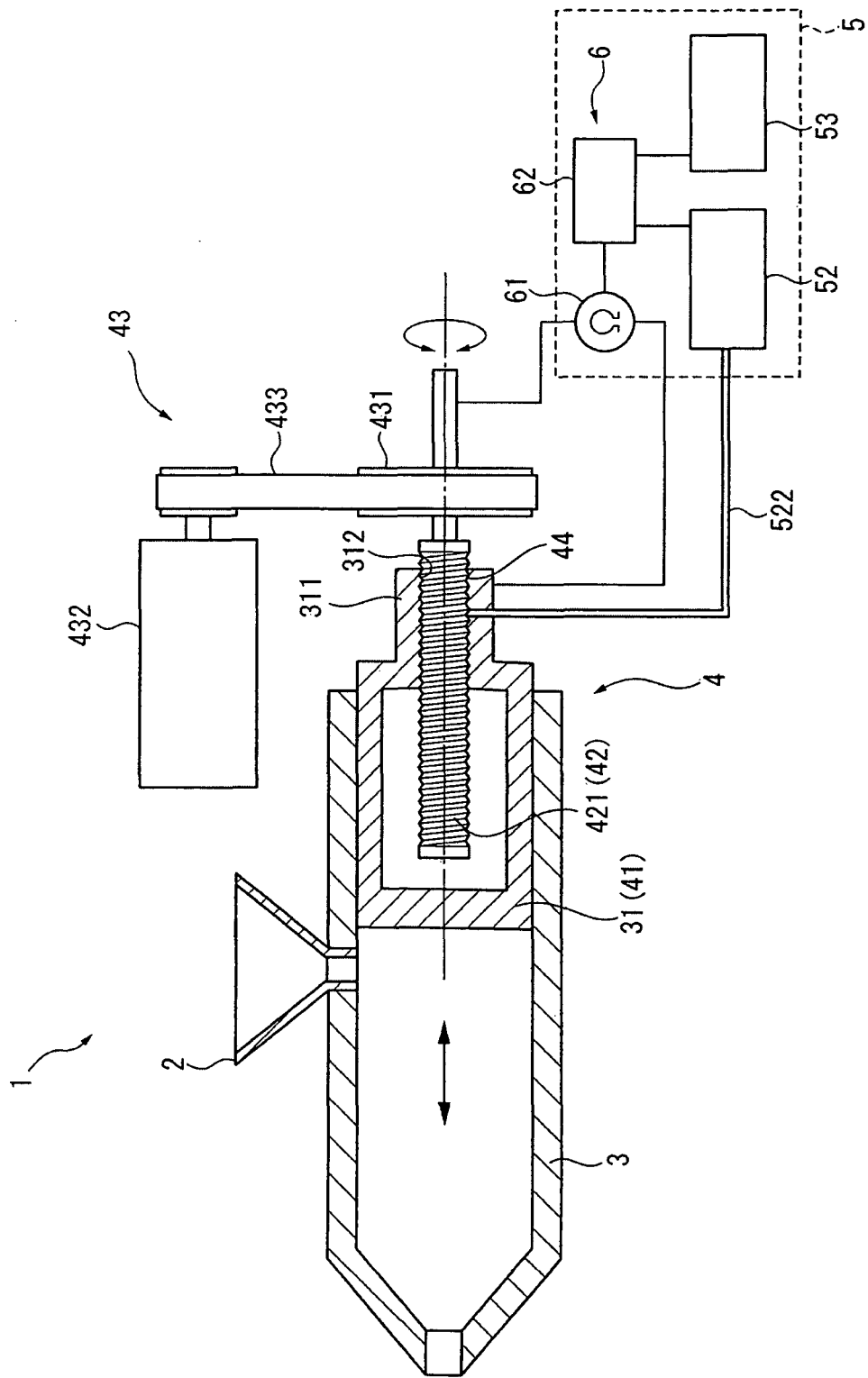
FIG. 1 is an illustration schematically showing an arrangement of an injection molding machine according to an embodiment.

FIG. 1 schematically shows an arrangement of an injection molding machine 1 according to the present embodiment.

As shown in FIG. 1, the injection molding machine 1 includes a driving mechanism 4 for injecting a molding material supplied into a cylinder 3 by a hopper 2, and a lubricant feeder 5 for detecting a lubricant shortage in the driving mechanism 4 to feed the driving mechanism 4 with the lubricant.

The driving mechanism 4 includes a fixed member 41, a movable member 42 that repeats a predetermined operation relative to the fixed member 41 at a predetermined cycle, a driver 43 for driving the movable member 42, and lubricant 44 for lubricating the movable member 42 between the fixed member 41 and the movable member 42.

The fixed member 41 also serves as a substantially-cylindrical metallic injection shaft 31 that is provided on an end of the cylinder 3 in a manner not rotatable around the shaft but axially slidable. An end of the injection shaft 31 opposite to the cylinder 3 is provided with a small-diameter section 311 in which a female screw 312 is formed.

The movable member 42 is a metallic screw shaft 421 screwed to the female screw 312 of the injection shaft 31.

The female screw 312 and the screw shaft 421 may not necessarily be typical screws but may be, for example, ball screws.

The driver 43 includes: a pulley 431 provided on the screw shaft 421 to be opposed to the injection shaft 31; a motor 432; and a belt 433 wound around the motor 432 and the pulley 431.

The motor 432 rotates the screw shaft 421 via the belt 433 and the pulley 431. The motor 432 inverts its rotary direction every predetermined number of rotation.

The lubricant 44 lubricates the rotation of the screw shaft 421 between the female screw 312 of the injection shaft 31 and the screw shaft 421.

Examples of the lubricant 44 are grease or oil.

The lubricant feeder 5 includes a lubrication-condition detector 6 for detecting the lubricant shortage in the driving mechanism 4, a feeder 52 for feeding the lubricant 44 to the driving mechanism 4 when the lubrication-condition detector 6 detects the lubricant shortage in the driving mechanism 4, and an alarm notifier 53 for notifying the lubricant shortage by alarm(s).

The lubrication-condition detector 6 includes a physical-quantity measuring unit 61 for continuously measuring physical quantity related to the driving mechanism 4, and a computer 62 for determining a presence of the lubricant shortage in the driving mechanism 4 based on the physical quantity measured by the physical-quantity measuring unit 61.

The physical-quantity measuring unit 61 is a measuring machine that measures electric current, electric resistance or electric potential difference between the injection shaft 31 and the screw shaft 421.

Figure 2:
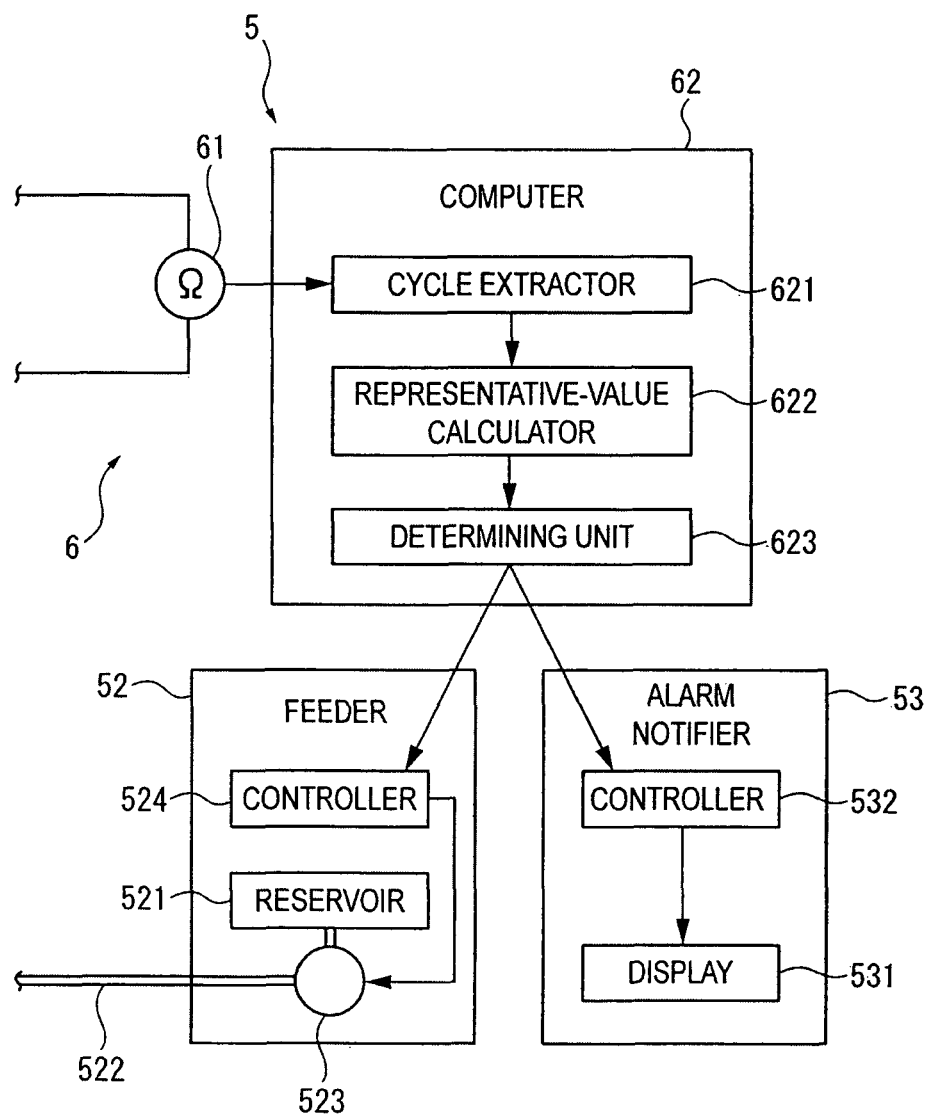
FIG. 2 is an illustration schematically showing an arrangement of a lubricant feeder of the injection molding machine according to the embodiment.

FIG. 2 schematically shows an internal arrangement of the lubricant feeder 5.

As shown in FIG. 2, the computer 62 includes a cycle extractor 621, a representative-value calculator 622 and a determining unit 623.

The cycle extractor 621 extracts a cycle datum per operational cycle of the screw shaft 421 from continuous data including the physical quantity measured by the physical-quantity measuring unit 61 and its measuring time.

The representative-value calculator 622 calculates a representative value for each of the cycle data extracted by the cycle extractor 621.

The determining section 623 determines a presence of the lubricant shortage in the driving mechanism 4 based on the plural representative values calculated by the representative-value calculator 622.

As shown in FIG. 2, the feeder 52 includes: a reservoir 521 for storing the lubricant 44; a pipe 522 provided between the reservoir 521 and the driving mechanism 4 (see FIG. 1) for feeding the lubricant 44 to between the injection shaft 31 and the screw shaft 421; a valve 523 provided on the pipe 522; and a controller 524 for controlling the valve 523.

The controller 524 opens and closes the valve 523 based on the determination by the determining unit 623 of the computer 62 to feed the lubricant 44 to the driving mechanism 4 via the pipe 522.

The alarm notifier 53 includes a display 531 for displaying the alarm(s) and a controller 532 for controlling the display 531.

The display 531 is a lighting section that displays the alarm(s) by lighting of luminescent diode. The controller 532 display the alarm(s) on the display 531 based on the determination by the determining unit 623 of the computer 62.

[Operation(s) of Injection Molding Machine]

Initially, supply of the molding material into the cylinder 3 by the hopper 2 is started.

Then, the motor 432 is driven. The motor 432 rotates the screw shaft 421 via the belt 433 and the pulley 431.

At this time, the injection shaft 31, which is screwed to the screw shaft 421, is not rotatable around the shaft but axially slidable. Accordingly, the injection shaft 31 axially slides by the rotation of the screw shaft 421.

Since the motor 432 inverts the rotary direction every predetermined number of rotation, the injection shaft 31 repeatedly advances and retracts axially within the cylinder 3.

Accordingly, every time the injection shaft 31 is reciprocated within the cylinder 3, a predetermined amount of the molding material is injected out of the cylinder 3.

[Operation(s) of Lubricant Feeder]

While the injection molding machine 1 is being operated, the physical-quantity measuring unit 61 can continuously measure electric current, electric resistance or electric potential difference between the injection shaft 31 and the screw shaft 421. Exemplifying an instance where electric resistance is measured, operation(s) of the lubricant feeder according to the present embodiment will be described.

Figure 3:
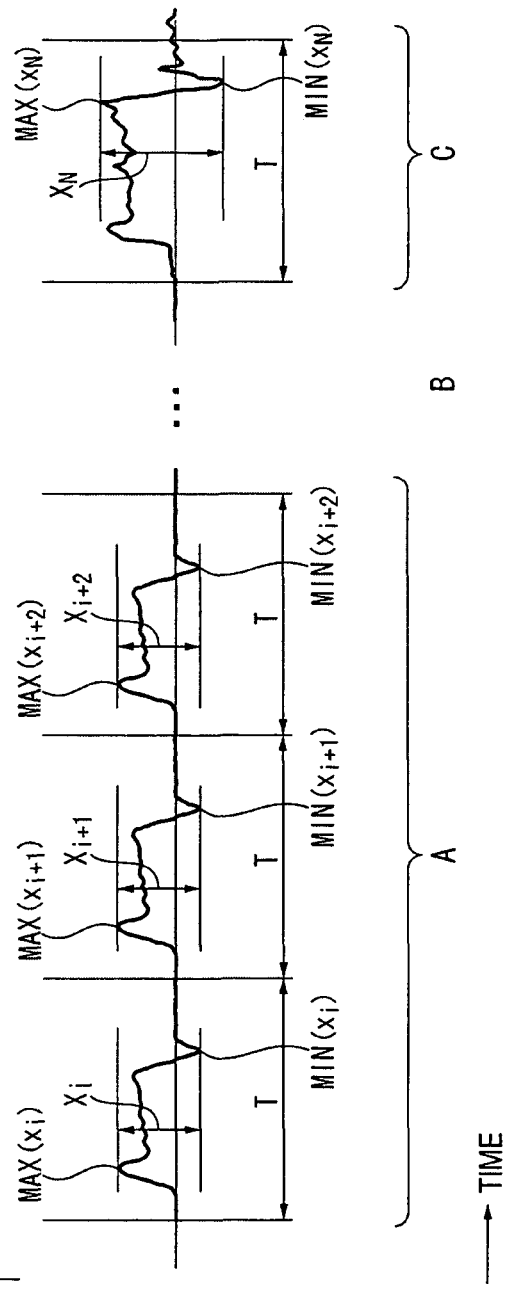
FIG. 3 is a graph showing time changes of physical quantity measured by a physical-quantity measuring unit of the injection molding machine according to the embodiment.

FIG. 3 shows time changes of electric resistance measured by the physical-quantity measuring unit 61.

In the graph of FIG. 3, the vertical scale represents value(s) of electric characteristics (electric resistance) while the horizontal scale represents time.

In the present embodiment, the injection shaft 31 (the fixed member 41) and the screw shaft 421 (the movable member 42) are metallic. Thus, when the screw shaft 421 is not operated, the members are in direct contact with each other, thereby exhibiting small electric resistance. On the other hand, when the screw shaft 421 is driven, the lubricant 44 is infiltrated between the female screw 312 of the injection shaft 31 and the screw shaft 421, such that the female screw 312 of the injection shaft 31 and the screw shaft 421 are insulated, thereby exhibiting large electric resistance.

In other words, the electric resistance measured by the physical-quantity measuring unit 61 changes depending on the operational state of the screw shaft 421.

Since the screw shaft 421 repeats rotation, operation suspension, and reverse rotation at a predetermined cycle (time T) in accordance with the inversion of the rotary direction conducted by the motor 432 every predetermined number of rotation, the electric resistance is also changed periodically.

A period A shown in FIG. 3 represents changes of the electric resistance when the lubrication condition is favorable. Since the screw shaft 421 repeats predetermined operations at a predetermined cycle (time T), a similar waveform of the electric resistance is repeatedly observed per time T.

In a period B, continuous driving of the driving mechanism 4 for a long time degrades the lubricant 44 and deteriorates the lubricity of the lubricant 44, such that the waveform of the electric resistance repeated per time T is gradually changed.

Then, as exemplarily shown in a period C, the waveform starts to be turbulent.

An exemplary cause of such turbulence of the waveform is that the lubricant 44 becomes less infiltrative between the female screw 312 of the injection shaft 31 and the screw shaft 421 due to the degradation of the lubricant 44, such that the electric resistance remains small even when the screw shaft 421 is rotated.

The cycle extractor 621 extracts the cycle datum per operational cycle of the screw shaft 421 from the continuous data whose entirety is shown in FIG. 3. Specifically, the cycle extractor 621 divides the continuous data into the cycle data per time T.

The representative-value calculator 622 calculates the representative value for each of the cycle data extracted by the cycle extractor 621. For instance, as the representative value $X_i$ of a cycle datum of "i" time, the representative-value calculator 622 calculates a variation value of the cycle datum. The variation value herein means a value obtained by subtracting the minimum value $MIN(x_i)$ from the maximum value $MAX(x_i)$ of the resistance $(x_i)$ in the cycle datum of "i" time, i.e., $X_i = MAX(x_i) - MIN(x_i)$.

Figure 4:
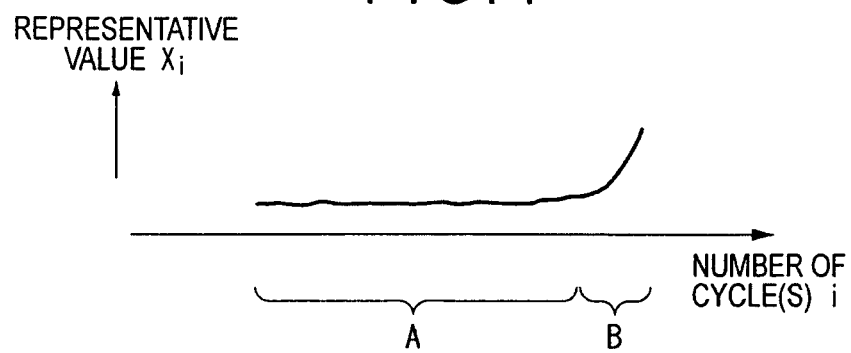
FIG. 4 is a graph showing changes of a representative value measured by a representative value calculator of the injection molding machine according to the embodiment.
Figure 5:
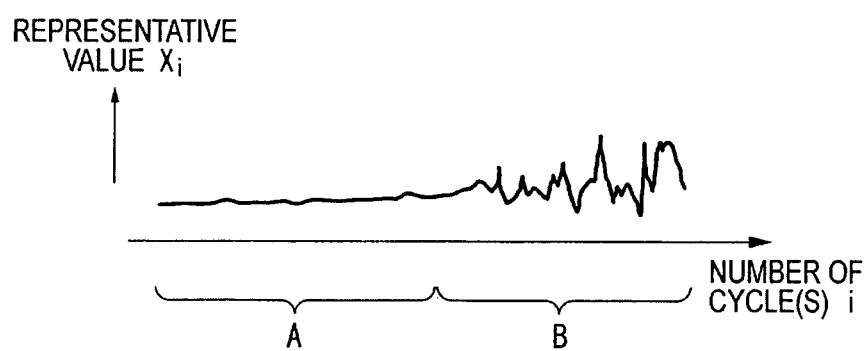
FIG. 5 is a graph showing changes of the representative value measured by the representative value calculator of the injection molding machine according to the embodiment.

FIGS. 4 and 5 show changes of the representative value $X_i$ measured by the representative-value calculator 622.

In the graphs of FIGS. 4 and 5, the vertical scales represent the representative value(s) $X_i$ while the horizontal scales represent the number of cycles (i).

Although the changes of the representative value $X_i$ are small when the lubricant condition is favorable as in the period A, the representative value $X_i$ is abruptly changed as in the period B of FIG. 4 or the representative value $X_i$ becomes unstable due to its continuous changes as in the period B of FIG. 5 when the lubricant 44 is degraded to deteriorates the lubricity due to continuous operations.

The determining unit 623 determines the lubricant shortage based on drastic changes of the representative value $X_i$ as in FIG. 4 or based on the instability of the representative value $X_i$ as in FIG. 5.

An exemplary method of determining the lubricant shortage based on the drastic changes is to set a threshold Y and determine the lubricant shortage when the representative value $X_i$ and the threshold Y satisfy a formula (1) as follows. It should be noted that a cycle of N time(s) is terminated immediately before the lubricant shortage is determined.

$$\left| \frac{1}{N} \sum_{i=1}^{N} X_i - \frac{1}{10} \sum_{i=N-10}^{N} X_i \right| > Y \tag{1}$$

An exemplary method of determining the lubricant shortage based on the instability of the representative value $X_i$ is to set a threshold Z and determine the lubricant shortage when the representative value $X_i$ and the threshold Z satisfy a formula (2) as follows. It should be noted that a cycle of N time(s) is terminated immediately before the lubricant shortage is determined.

$$\sum_{i=N-10}^{N} |X_i - X_{i-1}| > Z \tag{2}$$

As shown in FIG. 2, determination(s) of the lubricant shortage by the determining unit 623 are notified to the controller 524 of the feeder 52 and the controller 532 of the alarm notifier 532.

When receiving the determination of the lubricant shortage, the controller 524 of the feeder 52 opens the valve 523 and feeds the lubricant 44 stored in the reservoir 521 to the driving mechanism 4 via the pipe 522.

Feeding of the lubricant 44 by the feeder 52 solves the lubricant shortage of the driving mechanism 4, thereby terminating the notification from the determining unit 623. When the notification of the lubricant shortage from the determining unit 623 is terminated, the controller 524 closes the valve 523 to terminate feeding of the lubricant 4 to the driving mechanism 4.

However, when the notification of the determination of the lubricant shortage from the determining unit 623 is continued for a predetermined time period because, for instance, the lubricant 44 cannot be fed to the driving mechanism 4 with no lubricant 44 being stored in the reservoir 521, the controller 532 of the alarm notifier 52 displays the alarm by lighting the lighting section (the display 531).

[Effects and Advantages of Embodiment]

According to the present embodiment, the following effects can be obtained.

(1) Since the lubrication-condition detector 6 determines the presence of the lubricant shortage in the driving mechanism 4 based on the plural representative values $X_i$ calculated from the plural cycle data, the lubricant shortage of the driving mechanism 4, which repeats cycle operation(s), can be precisely detected.

(2) Since the determining unit 623 determines the presence of the lubricant shortage in the driving mechanism 4 based on time-series transition of the representative values of the continuous plural cycles, the lubricant shortage can be more precisely detected.

(3) Since the physical-quantity measuring unit 61 measures electric current, electric resistance or electric potential difference between the fixed member 41 (the injection shaft 31) and the movable member 42 (the screw shaft 421), the lubricant shortage in the driving mechanism 4 can be precisely detected based on the above elements.

(4) The lubricant feeder 5 including the lubrication-condition detector 6 can precisely detect the lubricant shortage in the driving mechanism, such that the feeder 52 can feed the driving mechanism 4 with the lubricant 44 without excess or shortage based on the detected lubricant shortage.

Accordingly, the lubricant feeder 5 according to the present embodiment can prevent problems such as heating, noises, vibration and burning of the driving mechanism 4 due to the lubricant shortage and pollution with the excessive lubricant around the driving mechanism 4.

(5) The lubricant feeder 5 including the alarm notifier 53 can notify and warn an operator of the lubricant shortage by an alarm.

The alarm notifier 53 does not issue an alert immediately after the lubrication-condition detector 6 detects the lubricant shortage in the driving mechanism 4 but issues an alarm when the lubricant shortage is continuously detected for a predetermined time period. Thus, an alarm can be issued when the lubricant shortage continued for a long time may lead to such problems as burning, heating, noises and vibration.

(6) The injection molding machine 1 including the lubricant feeder 5 can feed the driving mechanism 4 of the injection molding machine 1 with the lubricant 44 without excess or shortage by the lubricant feeder 5, thereby preventing problems such as burning, heating, noises and vibration of the driving mechanism 4.

[Modification]

The present invention is not limited to the embodiments described above but includes other arrangements as long as an object of the present invention can be achieved, which also includes the following modification(s).

(i) Although the physical-quantity measuring unit 61 exemplarily measures electric current, electric resistance or electric potential difference between the injection shaft 31 and the screw shaft 421 in the above embodiment, the arrangement is not limited thereto.

For instance, the physical-quantity measuring unit 61 may measure torque or electric current of the motor 432.

With this arrangement, the lubrication-condition detector 6 can also precisely detect the lubricant shortage based on the torque or the electric current of the motor 432, thereby providing the same excellent effects and advantages as in the above-described embodiment.

(ii) Although the representative value $X_i$ of the cycle datum is exemplarily the variation value obtained by subtracting the minimum value from the maximum value of the physical quantity ($x_i$) in the cycle datum in the above embodiment, the arrangement is not limited thereto.

For instance, the representative value may be the maximum value, the minimum value, an average value, an effective value or the like of the physical quantity in the cycle datum.

The effective value $X_{rms}$ is derived from a formula (3) as follows, using a physical quantity "x(t)" when a time "t" has passed since the cycle is started and a time "T" of one cycle.

$$X_{rms} = \sqrt{\frac{\int_0^T x^2(t)\,dt}{T}} \quad (3)$$

When the above value(s) is set as the representative value, the lubricity detector 4 can also precisely detect the lubricant shortage by suitably setting such conditions as a threshold value, thereby providing the same excellent effects and advantages as in the above-described embodiment.

(iii) The lubricant feeder 5 and the lubrication-condition detector 6 may not limitedly be used in the injection molding machine 1 but may be respectively used as separate devices.

For instance, the lubricant feeder 5 may be applied to another machine tool. Additionally, in an arrangement where the lubrication-condition detector 6 is employed as a separate body, an operator may manually feed the lubricant 44 to the driving mechanism 4 when the lubricant shortage is detected.

Also with such an arrangement, the separate devices respectively can provide the same excellent effects and advantages as in the above-described embodiment.

(iv) Although the alarm notifier 53 issues an alarm exemplarily when the lubricant shortage is detected continuously for a predetermined time in the above embodiment, the arrangement is not limited thereto.

For instance, the alarm notifier 53 may keep alarming an operator continuously from when the lubrication-condition detector 6 detects the lubricant shortage until when the lubrication-condition detector 6 no longer detects the lubricant shortage.

With this arrangement, an operator can be alarmed, thereby preventing problems such as burning, heating, noises and vibration of the driving mechanism 4.

(v) Although the portion to be detected by the lubricant feeder 5 and the lubrication-condition detector 6 is solely the driving mechanism 4 in the above embodiment, the arrangement is not limited thereto.

For instance, detection may be performed on plural portions.

In the above arrangement, the lubricant-condition detector 6 preferably detects the lubricant shortage of the plural portions separately, and the feeder 52 preferably feeds the lubricant 44 only to a portion where the lubricant shortage is detected among the plural portions.

With this arrangement, even when the injection molding machine 1 includes plural portions to be detected, the lubricant can be fed to the plural portions without excess or shortage.

The priority application Number JP2007-103773 upon which this patent application is based is hereby incorporated by reference.

What is claimed is:

1. A lubrication-condition detector that detects a lubricant shortage of a target portion, the target portion comprising: a fixed member; a movable member that repeats a predetermined operation relative to the fixed member at a predetermined cycle; a driver that drives the movable member; and a lubricant that lubricates the movable member between the fixed member and the movable member, the lubrication-condition detector comprising:

a physical-quantity measuring unit that continuously measures a physical quantity related to the target portion; and a computer that determines a presence of a lubricant shortage of the target portion based on the physical quantity measured by the physical-quantity measuring unit, wherein the computer comprises:

a cycle extractor that extracts for each operational cycle plural values of the physical quantity from continuous measurements of the physical-quantity measuring unit and a measuring time thereof, the plural values of the physical quantity being associated with the movable member as it moves through the operational cycle;

a representative-value calculator that calculates plural representative values for each of A plurality of operational cycles, each of the representative values being calculated from the plural values extracted by the cycle extractor for the corresponding operational cycle, wherein the representative value is one of a maximum value, a minimum value, an average value, an effective value or a variation value of the physical quantity measured in the operational cycle; and a determining unit that determines a presence of a lubricant shortage of the target portion based on the representative values calculated by the representative-value calculator for corresponding plural operational cycles.

2. The lubrication-condition detector according to claim 1, wherein the determining unit determines a presence of a lubricant shortage of the target portion based on time-series transition of the representative values of continuous plural cycles.

3. The lubrication-condition detector according to claim 2, wherein, the physical quantity measured by the physical-quantity measuring unit is electric current, electric resistance or electric potential difference between the fixed member and the movable member of the target portion.

4. The lubrication-condition detector according to claim 2, wherein the driver of the target portion comprises a motor for operating the movable member, and the physical value measured by the physical-quantity measuring unit is torque or electric current of the motor.

5. The lubrication-condition detector according to claim 1, wherein, the physical quantity measured by the physical-quantity measuring unit is electric current, electric resistance or electric potential difference between the fixed member and the movable member of the target portion.

6. The lubrication-condition detector according to claim 1, wherein the driver of the target portion comprises a motor for operating the movable member, and the physical value measured by the physical-quantity measuring unit is torque or electric current of the motor.

7. A lubricant feeder, comprising:
the lubrication-condition detector according to claim 1; and
a feeder that feeds the lubricant to the target portion when the lubrication-condition detector detects a lubricant shortage of the target portion.

8. The lubricant feeder according to claim 7, wherein
the lubrication-condition detector separately detects lubricant shortages of plural target portions, and
the feeder feeds the lubricant only to a target portion where a lubricant shortage is detected among the plural target portions.

9. The lubricant feeder according to claim 7, wherein an alarm notifier that notifies a lubricant shortage(s) of the target portion(s) detected by the lubrication-condition detector by an alarm.

10. An injection molding machine, comprising the lubricant feeder according to claim 7.

11. The injection molding machine of claim 10 wherein the determining unit determines a presence of a lubricant shortage of the target portion based on time-series transition of the representative values of continuous plural cycles.

12. The injection molding machine of claim 10, wherein, the physical quantity measured by the physical-quantity measuring unit is electric current, electric resistance or electric potential difference between the fixed member and the movable member of the target portion.

13. The lubricant feeder of claim 7 wherein the determining unit determines a presence of a lubricant shortage of the target portion based on time-series transition of the representative values of continuous plural cycles.

14. The lubricant feeder of claim 7, wherein, the physical quantity measured by the physical-quantity measuring unit is electric current, electric resistance or electric potential difference between the fixed member and the movable member of the target 15. A method of detecting lubrication condition for detecting a lubricant shortage of a target portion, the target portion comprising: a fixed member; a movable member that repeats a predetermined operation relative to the fixed member at a predetermined cycle; a driver that drives the movable member; and a lubricant that lubricates the movable member between the fixed member and the movable member, the method comprising:
continuously measuring a physical quantity related to the target portion;
extracting for each operational cycle plural values of the physical quantity from continuous measurements and a measuring time thereof, the plural values of the physical quantity being associated with the movable member as it moves through the operational cycle;
calculating representative values for each of a plurality of operational cycles, each of the representative values being calculated from the plural values extracted for the corresponding operational cycle, wherein the representative value is one of a maximum value, a minimum value, an average value, an effective value or a variation value of the physical quantity measured in the operational cycle; and
determining a presence of a lubricant shortage of the target portion based on the calculated plural representative values for corresponding plural operational cycles.

16. The method of detecting lubrication condition according to claim 15, wherein the presence of a lubricant shortage of the target portion is determined based on time-series transition of the representative values of continuous plural cycles.

17. The method of detecting lubrication condition according to claim 16, wherein the measured physical quantity is electric current, electric resistance or electric potential difference between the fixed member and the movable member of the target portion.

18. The method of detecting lubrication condition according to claim 16 wherein the driver of the target portion comprises a motor for operating the movable member, and the measured physical value is torque or electric current of the motor.

19. The method of detecting lubrication condition according to claim 15, wherein the measured physical quantity is electric current, electric resistance or electric potential difference between the fixed member and the movable member of the target portion.

20. The method of detecting lubrication condition according to claim 15, wherein the driver of the target portion comprises a motor for operating the movable member, and the measured physical value is torque or electric current of the motor.

* * * * *